United States Patent
Feser et al.

(10) Patent No.: US 9,110,004 B2
(45) Date of Patent: Aug. 18, 2015

(54) LABORATORY X-RAY MICRO-TOMOGRAPHY SYSTEM WITH CRYSTALLOGRAPHIC GRAIN ORIENTATION MAPPING CAPABILITIES

(71) Applicant: Carl Zeiss X-ray Microscopy, Inc., Pleasanton, CA (US)

(72) Inventors: Michael Feser, Orinda, CA (US); Christian Holzner, Wettringen (DE); Erik Mejdal Lauridsen, Haarlev (DK)

(73) Assignees: Carl Zeiss X-ray Microscopy, Inc., Pleasanton, CA (US); Xnovo Technology ApS, Køge (DK)

( * ) Notice: Subject to any disclaimer, the term of this patent is extended or adjusted under 35 U.S.C. 154(b) by 0 days.

(21) Appl. No.: 14/057,126

(22) Filed: Oct. 18, 2013

(65) Prior Publication Data
US 2014/0112433 A1    Apr. 24, 2014

Related U.S. Application Data

(60) Provisional application No. 61/715,696, filed on Oct. 18, 2012.

(51) Int. Cl.
*G01N 23/207* (2006.01)

(52) U.S. Cl.
CPC ........ *G01N 23/207* (2013.01); *G01N 2223/419* (2013.01); *G01N 2223/606* (2013.01)

(58) Field of Classification Search
CPC  G01N 2223/419; G01N 23/207; G01N 23/20
USPC .................................................. 378/70–90
See application file for complete search history.

(56) References Cited

U.S. PATENT DOCUMENTS

| | | | |
|---|---|---|---|
| 3,903,415 | A | 9/1975 | Holzapfel |
| 5,193,104 | A | 3/1993 | Bastie et al. |
| 5,491,738 | A | 2/1996 | Blake et al. |
| 7,130,375 | B1 | 10/2006 | Yun et al. |
| 7,443,953 | B1 | 10/2008 | Yun et al. |

(Continued)

FOREIGN PATENT DOCUMENTS

EP    2 775 296 A1    9/2014

OTHER PUBLICATIONS

Ludwig et al. (2009) "Three Dimensional Grain Mapping by X-ray Diffraction Contrast Tomography and the Use of Friedel Pairs in Diffraction Data Analysis," Review of Scientific Instruments, vol. 80:3 pp. 33905-33909.*

(Continued)

*Primary Examiner* — Courtney Thomas
(74) *Attorney, Agent, or Firm* — Houston & Associates, LLP

(57) ABSTRACT

A method and system for three dimensional crystallographic grain orientation mapping illuminates a polycrystalline sample with a broadband x-ray beam derived from a laboratory x-ray source, detects, on one or more x-ray detectors, diffracted beams from the sample, and processes data from said diffracted beams with the sample in different rotation positions to generate three dimensional reconstructions of grain orientation, position, and/or 3-D volume. A specific, cone beam, geometry leverages the fact that for a point x-ray source with a divergent beam on reflection of an extended crystal grain diffracts x-rays such that they are focused in the diffraction plane direction.

31 Claims, 5 Drawing Sheets

(56) References Cited

U.S. PATENT DOCUMENTS 7,978,821 B1 7/2011 Glavicic et al.
2012/0008736 A1 1/2012 Lauridsen et al.

OTHER PUBLICATIONS

International Search Report and Written Opinion of the International Searching Authority mailed Jan. 28, 2014, from counterpart International Application No. PCT/US2013/065584.

Ludwig, W. et al., "Three-dimensional Grain Mapping by X-ray Diffraction Contrast Tomography and the Use of Friedel Pairs in Diffraction Data Analysis," Review of Scientific Instruments, vol. 80:3, pp. 33905-33909, Mar. 19, 2009.

Lynch, P.A. et al., "A Laboratory Based System for Laue Micro X-ray Diffraction," Review of Scientific Instruments, vol. 78:2, pp. 23904-23910, Feb. 9, 2007.

Hofmann, F et al., "High energy transmission micro-beam Laue synchrotron X-ray diffraction", Materials Letters, Amsterdam, vol. 64, No. 11, Jun. 15, 2010.

Johnson, G. et al., "X-ray Diffraction Contrast Tomography: A Novel Technique for Three-dimensional Grain Mapping of Polycrystals. II. The Combined Case," Journal of Applied Crystallography, vol. 41, pp. 310-318, Jan. 16, 2008.

Knapic, M., "X-ray Diffraction Contrast Tomography," University of Ljubljana, Dept. of Physics, 13 pgs., May 28, 2011.

Ludwig, W. et al., "X-ray Diffraction Contrast Tomography: A Novel Technique for Three-dimensional Grain Mapping of Polycrystals. I. Direct Beam Case," Journal of Applied Crystallography, vol. 41, pp. 302-309, Jan. 16, 2008.

Robach, O et al., "A tunable multicolour rainbow filter for improved stress and dislocation density field mapping in polycrystals using X-ray Laue microdiffraction", ACTA Crystallograpy, vil. 98, No. 2, Mar. 1, 2013.

Stockmeier, M et al., "A focusing Laue diffractometer for investigation of bulk crystals", Journal of Applied Crystallography (2008), 41, 754-760.

International Preliminary Report on Patentability, mailed on Nov. 14, 2014, from counterpart International Application No. PCT/US2013/065584, filed on Oct. 18, 2013.

* cited by examiner

LABORATORY X-RAY MICRO-TOMOGRAPHY SYSTEM WITH CRYSTALLOGRAPHIC GRAIN ORIENTATION MAPPING CAPABILITIES

RELATED APPLICATIONS

This application claims the benefit under 35 USC 119(e) of U.S. Provisional Application No. 61/715,696, with the title Laboratory X-Ray Micro-Tomography System with Crystallographic Grain Orientation Mapping Capabilities, filed on Oct. 18, 2012, which is incorporated herein by reference in its entirety.

BACKGROUND OF THE INVENTION

Metals, ceramics and other important materials are composed of many individual single crystal grains. For homogenous composition materials, the crystal structure of all grains is identical, but their relative crystal orientation is not identical throughout the material. In fact many important engineering properties of materials are a function of the grain properties, such as grain size, boundaries, size distribution, and orientation, to list a few examples.

Single composition poly-crystalline materials typically have no contrast to identify individual grains and boundaries in conventional x-ray tomography scans based on absorption and/or phase contrast.

Electron backscatter diffraction imaging (EBSD) can be performed on the surface of polished cross-sections of materials in a scanning electron microscope to image grains and grain boundaries in two dimensions. The crystal orientation of grains is determined in EBSD. Serial sectioning with a focused ion beam milling tool and EBSD imaging can yield three dimensional (3-D) EBSD data. 3-D EBSD is a destructive measurement technique since the sample gets destroyed in the process, however.

Material evolution in the time domain as a function of external factors such as temperature cycling, stress or strain are extremely important to understand material failure and best processing conditions to yield materials with optimum properties. Since 3-D EBSD can only capture the grain map of a sample once, it is very unsatisfactory to study material evolution.

X-ray diffraction contrast tomography (x-ray DCT) is a non-destructive approach for obtaining the 3-dimensional characterization of polycrystalline microstructures. It allows the simultaneous mapping of the crystal grain shapes, grain orientation and microstructure of polycrystals that gives rise to absorption.

In the conventional x-ray DCT arrangement, the sample is illuminated with a monochromatic beam of high energy synchrotron radiation. As the sample is rotated, and grains pass through the illuminating beam, the condition for Bragg diffraction gets fulfilled by individual grains, these diffraction spots are recorded on a 2D detector placed behind the sample. The diffraction geometry is used to assign spots to the grains from which they arise, and to determine the crystallographic orientations of grains. The spots are used as projections of the grains to reconstruct the respective grain shapes. The technique has been applied to several materials science investigations, for example in the 3D characterization of grain boundary networks, and in-situ studies of inter-granular stress corrosion cracking in some stainless steels. Other materials investigated by x-ray DCT have included aluminum alloy Al 1050. Most importantly, it is now possible to perform routine 3-D grain map measurements non-destructively, which enables repetitive measurements to study time evolution.

The necessity to use synchrotron sources to perform these measurements is very limiting and a laboratory source diffraction CT system would close this gap. It is well known that synchrotrons generate x-rays with orders of magnitude higher brightness than laboratory sources, and the methods for DCT developed for the synchrotron require high beam brightness, which manifests itself in high beam collimation and monochromaticity.

Laboratory sources generally have very poor brightness compared to synchrotrons since they emit a very wide bandwidth of x-ray wavelengths in terms of Bremsstrahlung. Characteristic emission lines emitted in addition to the Bremsstrahlung background are low in intensity compared to total x-ray power emitted, and the use of a monochromator (crystal monochromator or multilayer) further reduces the intensity when trying to monochromatize the beam of a laboratory source.

Nevertheless, U.S. Patent Application Publication No. 2012/0008736A1, to Lauridsen et al., published on Jan. 12, 2012, describes an x-ray DCT system that can use a laboratory source. This system mirrors the implementation of a synchrotron DCT setup, in that it assumes the use of a focused and monochromatic x-ray beam. Additionally a scheme using non-standard detectors is described to detect the diffracted signal.

SUMMARY OF THE INVENTION

A problem with proposed configurations for laboratory-source x-ray DCT systems is that their performance should be low. Since they require a focused, monochromatic beam, the resulting x-ray flux from existing laboratory x-ray sources should be too low, resulting in impractically long exposure times.

A need continues to exist, therefore, for methods and systems capable of performing x-ray DCT analysis in the laboratory. In particular, a need exists for techniques that make it possible to use x-ray DCT in research and industrial facilities that do not have a synchrotron radiation source. Also particularly needed are arrangements that utilize simple and effective detection systems.

In general, according to one aspect, the invention features a method for three dimensional crystallographic grain orientation mapping. In the method, a rotating sample is illuminated by a broadband, cone x-ray beam derived from a laboratory x-ray source, to generate, on an x-ray detector, a diffracted beam image. Data from the image coupled with information regarding an angle of sample rotation are processed (e.g., by a controller) to obtain three dimensional reconstructions of grain orientation and position.

According to another aspect, the invention features an apparatus for three dimensional crystallographic grain orientation mapping. The apparatus includes a laboratory x-ray source, one or more optional x-ray conditioning devices such as apertures for restricting the extent of the cone beam from the source, a stage for rotating the sample, a single detection system, preferably a high resolution pixilated x-ray detector, for collecting diffraction data, and a controller for processing data received by the detector, coupled with information regarding an angle of sample rotation, to generate three dimensional reconstructions of grain orientation and position.

Utilizing the apparatus and techniques described herein, crystallographic mapping using x-ray DCT principles can be performed in the laboratory with one of the primary advantages of the present system being its compact size. Compared with the synchrotron x-ray sources typically needed in traditional x-ray DCT experiments, the laboratory x-ray source used here is small, much less expensive, and allows constant access. Furthermore, in contrast to previous approaches, a broadband, unfocused (cone) x-ray beam is used that more efficiently utilizes the x-rays produced by a standard laboratory source.

The above and other features of the invention including various details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
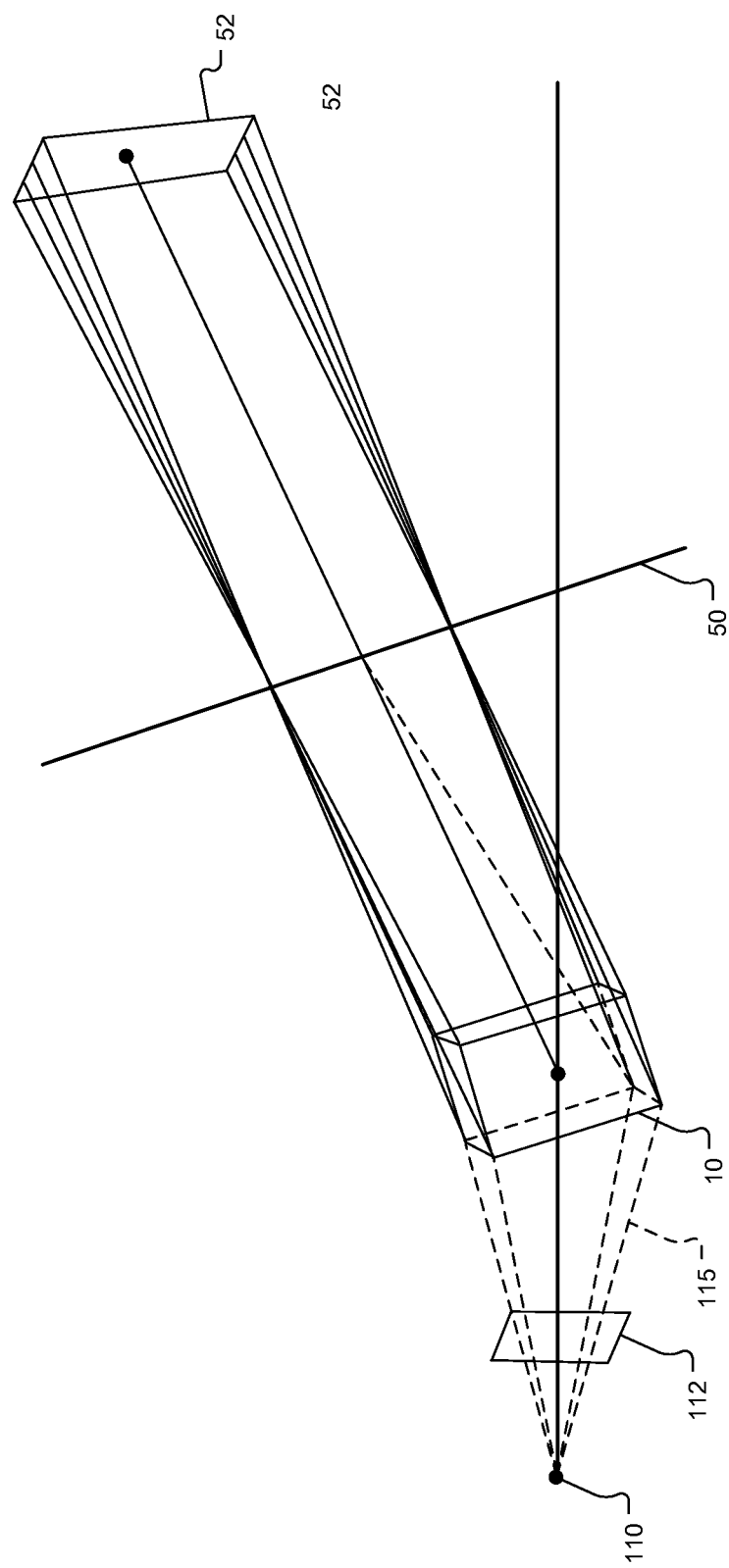
FIG. 1 is a schematic perspective view showing the Laue focal plane 50 and the projection plane 52 that are generated when x-rays from a broadband source illuminate one grain of a crystalline sample through an aperture.

The current embodiment generally relates to a method and apparatus for obtaining three dimensional crystallographic grain orientation mapping. In contrast to previously described approaches, the system, and corresponding method, uses a laboratory x-ray source and a detection system, which is able to detect the x-rays transmitted through and diffracted by the sample at preferably at least two distances from the sample in a conebeam geometry. Preferably, a high resolution pixilated x-ray detector is used to collect diffracted x-rays and generate diffraction data. A lower resolution detector is used to detect the diffracted x-rays and projection images through the sample in the projection plane.

During operation, the sample being studied is rotated utilizing, for instance, a motion stage system with an angle of rotation (θ), to produce a series of angular projections. A controller receives image data of multiple images from the detection system (obtained while rotating the sample) and performs three dimensional reconstructions of grain orientation and position.

Preferably, the system uses a "white" or broadband beam of x-ray radiation, i.e., a beam with a wide wavelength spectrum. The bandwidth of the x-ray beam is only restricted by the operating voltage of the x-ray source and optional absorption filters in the beam.

It is well known that a broadband (white) x-ray beam gives rise to diffraction patterns. For a single crystal/grain, this is referred to Laue diffraction patterns. Diffraction reflections manifest themselves at specific angles corresponding to 1) the d-spacing of the crystal planes, 2) the orientation of the planes and 3) one specific x-ray energy or narrow range of x-ray energy that is selected from the incoming broad-band x-ray spectrum to fulfill the Bragg condition for reflection.

In polychromatic diffraction, each reflection off the crystal "selects" a specific wavelength or narrowband from the incident wavelength spectrum. Generally many reflections of one crystal grain are present in a single diffraction pattern corresponding to various crystal plane d-spacings, diffraction angles and x-ray wavelengths obeying the Bragg condition $2d^*\sin(\beta)=\text{lambda}$, (or: $2d\cdot\sin\beta=\lambda$), where d is the lattice spacing, beta ($\beta$) the diffraction angle and lambda ($\lambda$) the wavelength.

For a single crystal material, a system controller analyzes these diffraction patterns and the images detected by the detector system and extracts crystal orientation and lattice spacing from the data.

In a polycrystalline material that has many grains illuminated by the x-ray beam, each grain will contribute many reflections to the diffraction patterns. The polychromatic diffraction pattern of a polycrystalline sample using a collimated (parallel) incident x-ray beam in general leads to a superposition of many diffraction spots for which it is not possible to decipher crystal grain association, wavelength and d-spacing. In fact, if a large number of grains are present, the random orientation of the individual grains will give rise to so called Laue diffraction rings, which are well known in a diffraction method called powder diffraction. Powder diffraction is an established method to determine the crystal structure of a material, but does not reveal any specific grain information.

In contrast, the present system uses a specific (cone beam) geometry that leverages the fact that for a point x-ray source with a divergent beam on reflection of an extended crystal grain diffracts x-rays such that they are focused in the diffraction plane direction to a distance equal to the source-sample distance dss. We call this special plane the Laue focusing plane. This focusing effect is caused by the single crystal grain "seeing" the x-ray source under different incidence angles over the extent of the crystal grain, which then selects different wavelengths and diffraction angles for the reflection according to the aforementioned Bragg's law.

Different from collimated (parallel) beam polychromatic diffraction, the wavelength of the reflected x-rays is not constant across one grain in the present system, but varies dependent on the position within the grain where the x-rays strike.

FIG. 1 illustrates the Laue focal plane 50 and the projection plane 52.

In more detail, a broadband source 110 emits a diverging beam of broadband radiation 115. This radiation is diffracted by a crystal or grain within the sample 10.

The diffraction effect by the crystal 10 yields the Laue focal plane 50 where the x-rays that meet the Bragg condition are focused by the diffraction in the crystal or grain 10 of the sample. Since the focusing only occurs in the diffraction plane, in general the pattern of the diffracted beam will form a line in the Laue focal plane. It is also noted that the distances between source and sample (dss) and between sample and the Laue focal plane (dsd1) are equal. Then, at a further distance from the sample 10, the projection plane 52 is found from the projection of the diffracting crystal or grain. The distance of the projection plane from the Laue focal plane is arbitrary and depends on the pixel size of the x-ray detector available to record the pattern in the projection plane.

Figure 2A:
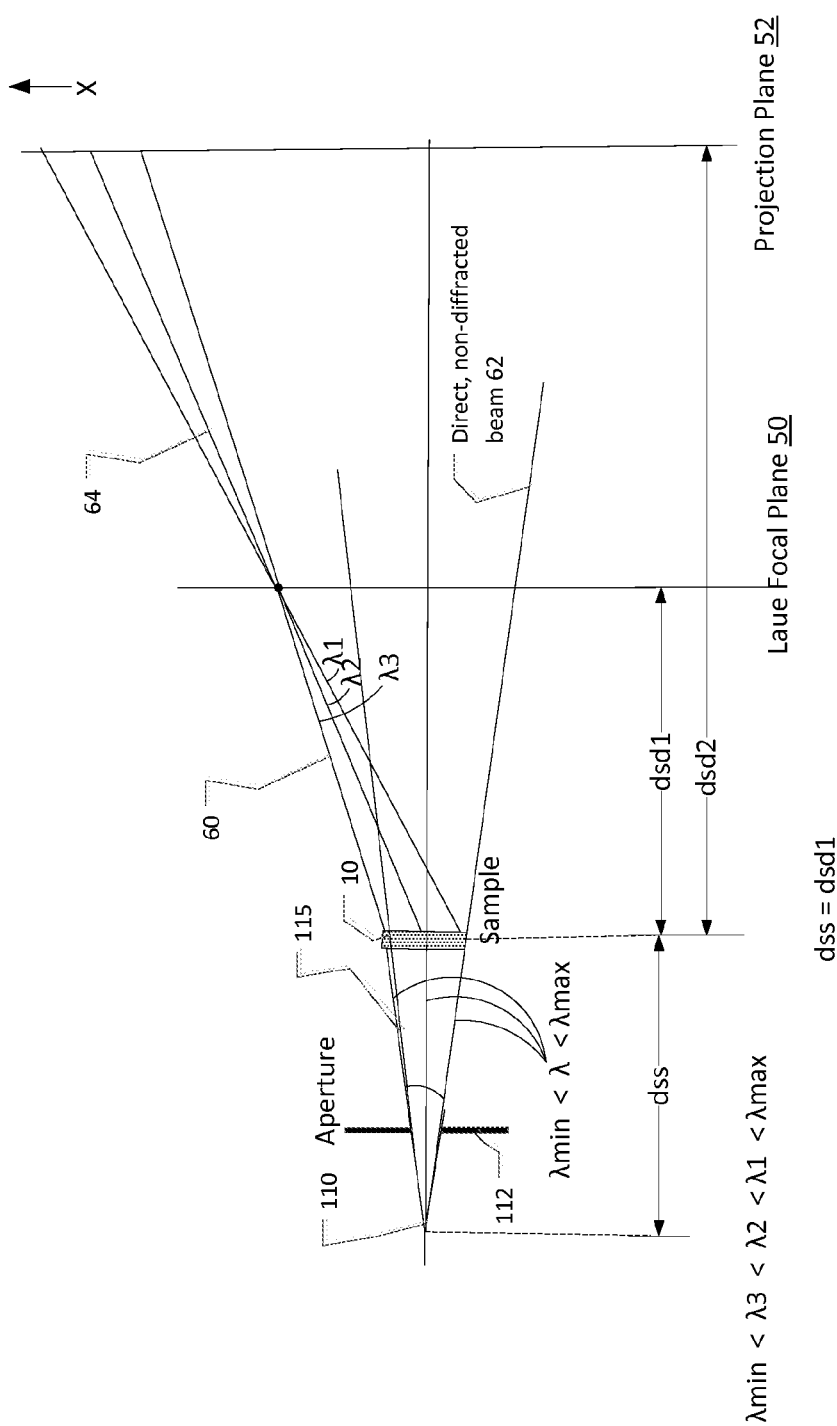
FIG. 2A is a side view showing the relevant distances in the set-up of FIG. 1.

FIG. 2A is a top view showing the relevant distances when a broadband diverging beam is diffracted by a sample crystal grain. Specifically, the distance between the source 110 and the sample 10 is dss. The distance between the sample 10 and the Laue focal plane 50 is dsd1 and the distance between the sample 10 and the projection plane 52 is dsd2.

Of interest is the fact that different wavelengths or energies within the x-ray beam 115 meet the Bragg condition along different portions of the sample crystal or grain 10. Thus, the features generated at the Laue focal plane 50 are combination of multiple wavelengths, $\lambda 1$, $\lambda 2$, $\lambda 3$. These wavelengths are within the spectral band $\lambda$min to $\lambda$max contained within the broadband x-rays emitted by the source 110.

An aperture 112 is used between the source 110 and the sample 10 to restrict the illumination beam on the sample and separate the direct transmitted beam/non-diffracted beam 62, from the diffracted beam 60, 64.

Since the diffracted beam 60, 64 is focused in the Laue plane, the projected image of the crystal in the projection plane is inverted and has a geometrical magnification that is given by (dsd2−dss)/dss, and can also appear sheared.

Figure 2B:
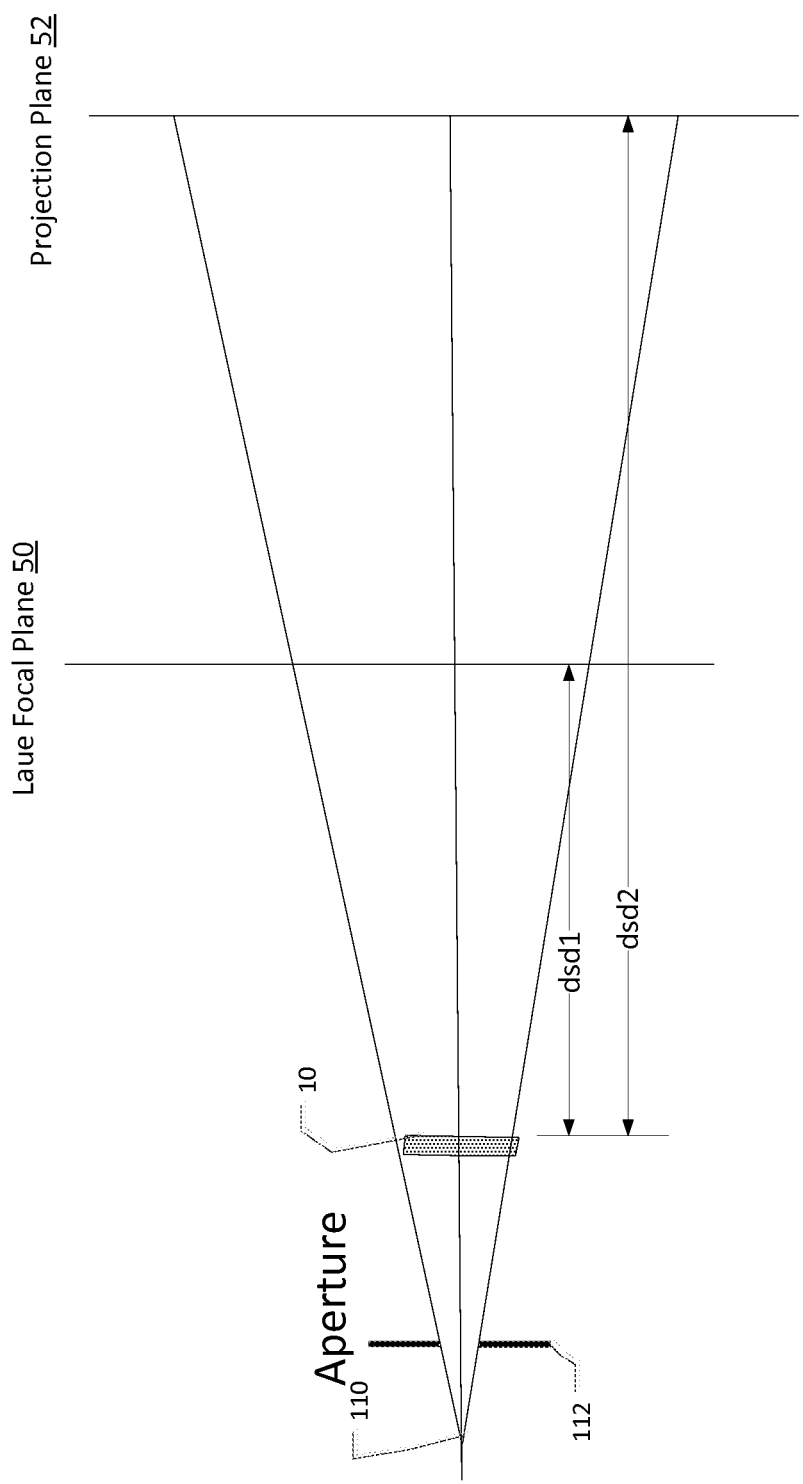
FIG. 2B is a top view showing the relevant distances in the set-up of FIG. 1.

FIG. 2B is a top view showing the relevant distances when a broadband diverging beam is diffracted by a sample crystal grain. The focusing effect at the Laue focal plane 50 leads to the formation of line-shaped spots.

The appearance of the diffracted signals as line-shaped spots in the Laue focal plane comes from a focusing effect and a magnification effect. One such line shaped spot originates from the diffraction of X-rays off one set of planes within one crystal grain of the sample. The crystal planes within the grain diffract and focus the X-rays along their normal direction to a narrow line. This focusing effect occurs across the whole length of the crystal grain, which means that the length of the line shaped spot in the Laue focal plane is a projected representation of the diffracting grain's physical size in this direction magnified by a factor of (dss+dsd1)/dss, which is equal to 2. The grain is projected non-inverted in this direction. From this it becomes clear that in order to be able to resolve crystal dimensions in the Laue focal plane a high-resolution detector will be required, which is able to resolve the grain dimensions since the geometric magnification is very low and equal to two. The magnification of the projection of the grain in the projection plane is given by (dss+dsd2)/dss which is identical to projection x-ray imaging systems. The larger geometrical magnification in the projection plane enables the use of lower resolution x-ray detector systems.

Figure 3B:
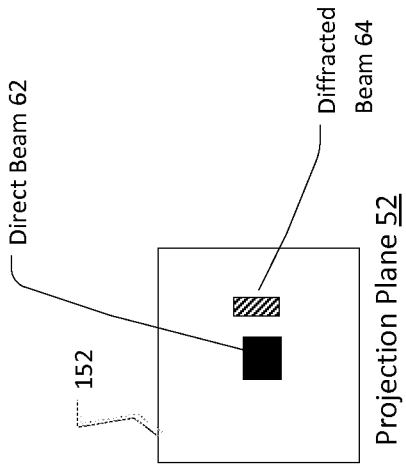
FIG. 3B illustrates the image generated at the projection plane and the relationship between the direct beam in the diffracted beam.
Figure 3A:
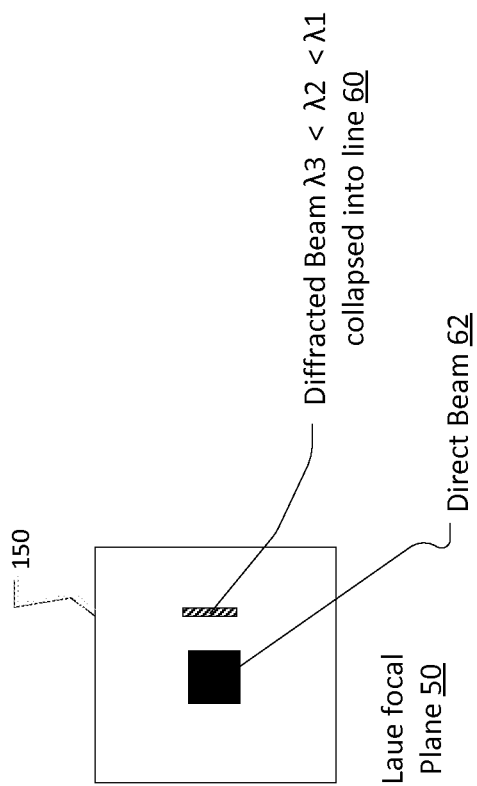
FIG. 3A illustrates the image generated at the Laue focal plane and relationship between the direct beam and the diffracted beam.

For example, as illustrated in FIG. 3A, a spatially resolved x-ray detector 150 located at the Laue focal plane 50 detects the lines 60 that encode the orientation of the plane of the reflection. The lines 60 at the Laue focal plane 50 are adjacent to any x-rays that form the direct beam 62 that are not diffracted by the sample 10.

As illustrated in FIG. 3B, a spatially resolved x-ray detector 152 located at the projection plane 52 detects reflected x-rays 64 onto a projection plane detector 152 that give rise to a projection of the diffracting grain.

In the projection plane, the magnification of the projection of the grain is not equal in the diffraction and orthogonal plane. In the diffraction plane the projection is inverted and has a lower magnification than in the orthogonal plane. In the orthogonal plane, the projection is non-inverted.

One strategy to obtain a re-projection of the grain outline into the sample plane for the reconstruction of a 3-D grain map is to re-project the grain shape from the projection plane through the line focus in the Laue focal plane 52. This allows for the identification of the index and wavelength giving rise to the reflection, knowing the geometry of the setup (source position) along with inferences as to the exact grain location within the sample.

The identification of Friedel pairs in the diffraction data aids in the identification of diffraction signals belonging to the same grain.

Figure 4:
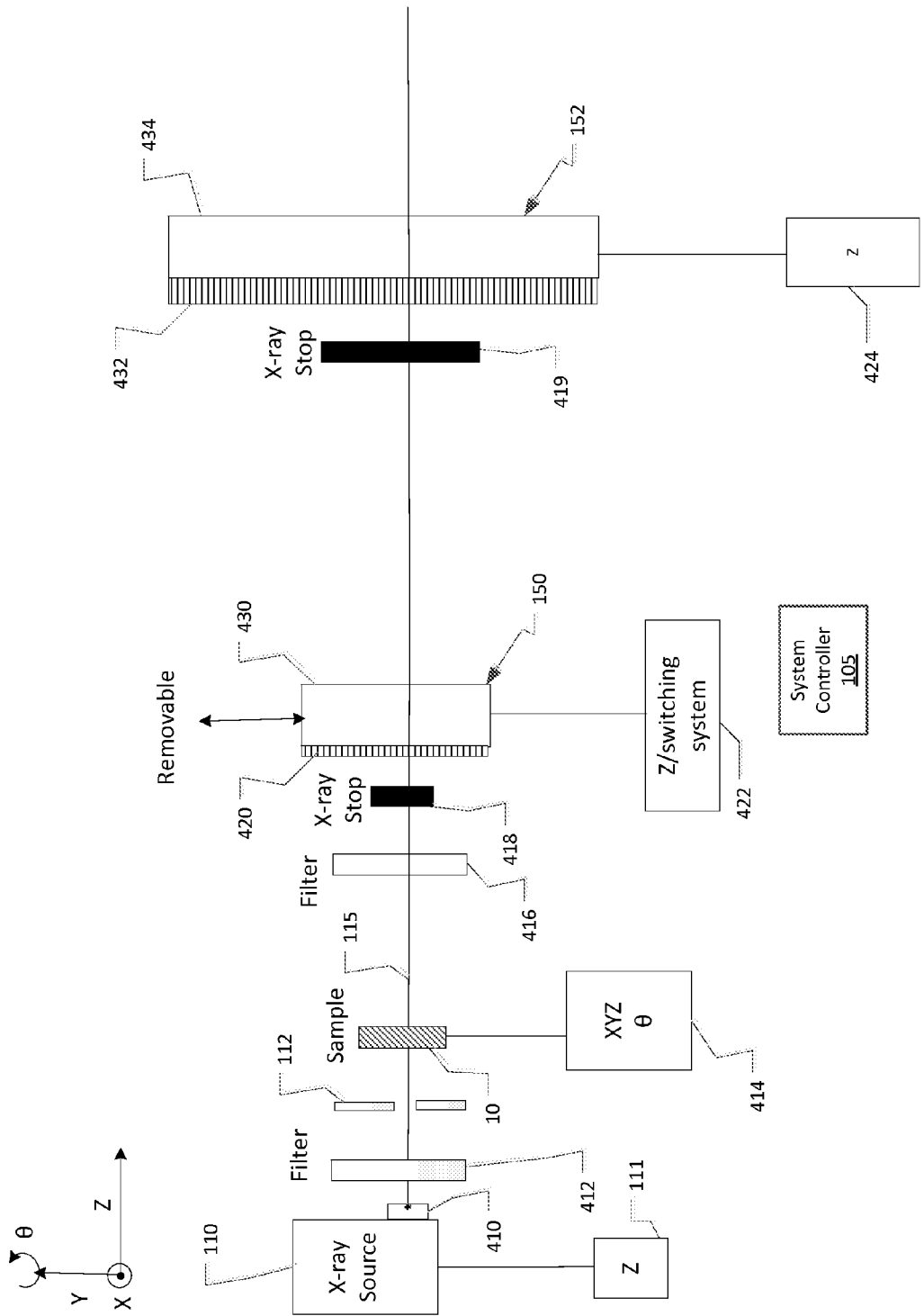
FIG. 4 is a schematic diagram showing an x-ray and detector system of an apparatus that can be used to conduct x-ray DCT according to principles of the invention.

Shown in FIG. 4 is one example of an apparatus for conducting x-ray three dimensional crystallographic grain orientation mapping according to embodiments of the invention. The apparatus generally includes the x-ray source 110, for illuminating sample 10.

The source 110 is a "laboratory x-ray source". It is preferably located on a source z-axis stage that enables independent adjustment of source to sample distance (dss). As used herein, a "laboratory x-ray source" is any suitable source of x-rays that is not a synchrotron x-ray radiation source.

Source 110 can be an X-ray tube, in which electrons are accelerated in a vacuum by an electric field and shot into a target piece of metal, with x-rays being emitted as the electrons decelerate in the metal. Typically, such sources produce a continuous spectrum of background x-rays combined with sharp peaks in intensity at certain energies that derive from the characteristic lines of the selected target, depending on the type of metal target used. Furthermore, the x-ray beams are divergent and lack spatial and temporal coherence.

In one example, source 110 is a rotating anode type or microfocused source, with a Tungsten target. Targets that include Molybdenum, Gold, Platinum, Silver or Copper also can be employed. Preferably a transmission configuration is used in which the electron beam strikes the thin target 410 from its backside. The x-rays emitted from the other side of the target are used as the beam 115.

In another, more specific example, source 110 is a structured anode x-ray source such as described in U.S. Pat. No. 7,443,953 issued to Yun, et al. on Oct. 28, 2008, the contents of which are incorporated herein by reference in their entirety. In this case, the source has a thin top layer made of the desired target material and a thicker bottom layer made of low atomic number and low density materials with good thermal properties. The anode can include, for instance, a layer of copper with an optimal thickness deposited on a layer of beryllium or diamond substrate.

X-ray lasers producing radiation having an energy suitable for the tomographic applications described herein also can be employed.

In still another example, the source 110 is a metal jet x-ray source such as are available from Excillum AB, Kista, Sweden. This type of source uses microfocus tubes in which the anode is a liquid-metal jet. Thus, the anode is continuously regenerated and already molten.

The x-ray beam 115 generated by source 110 is preferably conditioned to suppress unwanted energies or wavelengths of radiation. For example, undesired wavelengths present in the beam are eliminated or attenuated, using, for instance, an energy filter 412 (designed to select a desired x-ray wavelength range (bandwidth)). Nevertheless, the filter 412 does not substantially reduce the total energy or bandwidth of the transmitted beam 115. For example, the filter 412 preferably decreases the power in the beam by no greater than 50%. In the preferred embodiment, it decreases the power in the beam by no greater than 30%. The relevance is that most of the broadband x-rays generated by the x-ray source 110 are preserved to illuminate the sample 10. In general the bandwidth of the x-rays used are greater than 40% as defined by the ratio of the central x-ray energy to the full width half maximum (FWHM) of the x-ray energy band. E.g. for a central energy of 50 keV an energy band of at least 20 keV around the central energy is used. In general the bandwidth is at least 20%, since otherwise the available flux of the source is cut too severely. It is also recognized that by collecting data with various x-ray source/filter combinations, the central energy and bandwidth are varied in some examples. This provides additional information in the data that can be used by the control system 105 to identify the wavelength range of recorded reflections.

The beam extent is preferably reduced by passing the x-ray beam through aperture device 112, having a beam defining pinhole or appropriate square aperture. This aperture limits the illuminated region on the sample 10 and restricts the size of the direct beam on the x-ray detection system. It is recognized that by using different size apertures the number of crystal grains within the beam can be adjusted, which is advantageous to keep the number of diffraction reflections manageable and reduce overlap of reflections. In general, every grain will already have several reflections recorded in the Laue and projection planes.

More than one energy filter 412 and/or aperture device 112 are employed in other implementations. On the other hand, this beam conditioning is omitted in cases in which the laboratory source (e.g., a laser) generates an adequately bandlimited and/or spatially limited beam.

The x-ray beam 115 derived (either directly, i.e., without further conditioning, for example in the case of a laser source, or conditioned as described above) from the laboratory x-ray source 110 illuminates sample 10, the sample being studied. Often, the sample 10 is a polycrystalline material having many crystal grains in which each grain constitutes a crystal with translational symmetry. While the grains can have the same chemical composition and lattice structure, they generally have different orientations.

Examples of materials that can be analyzed using the apparatus and techniques described herein include but are not limited to metals, metal alloys, ceramics, and so forth.

The region of interest of the sample 10 is located in the beam using the x, y, z axis translatory capability of the sample stage 414. The sample 10 is then rotated (see angle θ) around the y axis exposing different sample faces to the incoming x-ray beam 115. In specific examples, the sample 110 is held in a sample holder mounted on a stage 414 (not shown) which allows rotation and, in preferred implementations, translation of the sample in relation to the x-ray beam 115 to allow for alignment.

For instance, the sample 10 can be manipulated using a conventional system, which includes a sample holder and a stage system, ideally motorized, for adjusting and rotating the sample 10. The stage 414 may be designed for translation along (z-axis) and/or in the transverse directions (y and x axes) of the x-ray beam 115 illuminating the sample 10, in the plane of the optical table (x-axis) and/or in a direction vertical to it (y-axis). For convenience, the coordinate system used herein has as the z-axis the axis along optical path defined by the incoming x-ray beam; the x-axis as perpendicular to the incoming x-ray beam 115 (in the plane of the optical table); and the y-axis as projecting in a direction perpendicular (vertical) with respect to the (horizontal) plane of the optical table.

In one example, the sample stage 414 is controlled by a system controller 105 and has a central, rotational axis y and the position of the sample can be adjusted so that this rotational axis y is perpendicular to the direct path of the x-ray beam 115. The stage 414 can rotate sample 10 about rotational axis y (see angle θ in FIG. 4) either with a predefined, settable rotational speed such as in the range from 20 minutes to 24 hours per full rotation of 360° or in stepwise, incremental rotational movements that may be set such as in the range from 0.01° to 15° per incremental rotation. The stage can have a default reference point for the rotational position of 0° and can provide an option for setting an actual reference point at initiation of the rotational movement of a mounted sample. The rotational angle of the stage with respect to the reference point is communicated from the sample staging device 414 to the system controller 105.

For instance, the sample 10 can be held on a sample holder, which projects from a base of the stage 414. The base can translate in the x-z plane under control of an x-z sample motion stage, allowing fine positioning of the sample on the plane of the optical table.

A sample rotation stage rotates the sample motion stage thus also the sample 10 in the x-ray beam 115, around an axis of rotation extending parallel to the y-axis. An x-axis sample motion stage can be provided for relatively large or gross positioning of the sample along the x-axis, allowing, for instance, the loading of the sample. A y-axis (translational) sample motion stage also can be provided for height adjustments of the sample 10 in the x-ray beam 115 relative to the top of the optical table.

Interaction of the incoming x-ray beam with the rotating sample generates a series of angular projections 60 (see FIG. 3A) captured on the scintillator 420 of the Laue plane x-ray detector 150. An x-ray stop 418 is preferably provided to block or attenuate the direct beam from the x-ray source 110. The advantage of blocking the direct beam using the x-ray stop 418 is that the direct beam carries little information about the grain structure of the sample 10. Moreover, since its signal strength is much stronger than any diffracted beam, blocking the direct beam improves the performance of the Laue plane x-ray detector 150 and reduces stray light generated in the scintillator 420. In general, the size of the x-ray stop 418 is larger than the aperture 112 due to the diverging characteristic of the x-ray beam 115.

The x-ray stop 418 is selected to be partially transmissive to still collect an absorption contrast projection of the sample 10 on the scintillator 420 in some examples. This direct image is useful in reconstructing the outline of the sample and determining the center of mass of the sample 10 by the controller 105.

In some implementations, a further filter 416 is located between the sample 10 and the scintillator 420. This can be used to filter out any unwanted energies in the x-ray beam.

In either case, the incoming diffraction x-ray beam 60 and transmitted (or extinction) x-ray beam 62 (if not blocked) are converted by the scintillator 420 of the Laue plane x-ray detector 150 into photons of lower energy (typically within the visible range of the electromagnetic spectrum). In turn, the lower energy (typically in the visible region) photon beams emitted from transmitted x-ray image 62, if present, and from the diffracted x-ray image 60 are further handled by an optical portion 430 of the Laue plane x-ray detector 150.

The optical portion 430 of the Laue plane x-ray detector 150 typically includes an optical magnification lens system and a detector, e.g., one using a suitable film or a camera detector based on a charge coupled device (CCD) or CMOS sensor. The image generated by the detector is provided to the system controller 105.

The optical portion 430 is preferably optically disposed downstream from scintillator 420. The optical portion 430 preferably includes a magnification lens held within a housing. Two couplets can be used to condition the optical signal from the magnification lens. A final tube lens couplet forms images on the detector (e.g., a CCD camera).

In some examples, a turning mirror is included in the optical portion of the Laue plane x-ray detector 150. It is located prior to the lenses to avoid damage from the x-rays and allow any remaining x-rays to travel on to the subsequent projection plane x-ray detector 152. In the current embodiment, the Laue detector 150 is removed to take images on the projection plane detector 152. This is accomplished by the system controller 105 switching out the detector 150 using a x or y-axis motion stage/switching system 422.

In general, suitable arrangements that can be used are described, for instance, in U.S. Pat. No. 7,130,375 B1, issued to Yun et al. on Oct. 13, 2006, the contents of which are incorporated herein by reference in their entirety.

The Laue plane x-ray detector 150 is mounted utilizing the Z-axis motion stage/switching system 422 that further enables adjustment of the position of the Laue plane x-ray detector 150 in the x, y and/or z directions.

In specific examples, the source to sample distance dss (in the z direction) is between 5 millimeters (mm) to 50 cm. The sample to Laue detector distance dsd1 (also in the z direction) can be between 5 mm to 50 cm.

In one configuration, the thickness of scintillator material 420 is between 50 µm and 1 millimeters (mm). It employs cesium iodide (CsI), cadmium tungstate (CdWO4) and so forth. The optical portion 430 then provides magnification of about 0.4× or more. In another implementation, thickness of scintillator is between 10 µm and 500 µm, with the optical portion 430 providing a magnification of 4×. In a further implementation, a thinner scintillator 420 of between 5 µm and 250 µm is used with the optical stage 430 providing a magnification of 10×. A thickness of 2 µm to 200 µm and an optical portion providing a magnification of 20× or more can be used as well. In yet other examples, the optical portion 430 provides for magnification of about 50× or less.

Interaction of the incoming x-ray beam with the rotating sample also generates a series of angular projections 64 captured on the scintillator 432 of the projection plane x-ray detector 152. A second x-ray stop 419 is preferably provided to block the direct beam from the x-ray source 110. Here again, the advantage of blocking the direct beam using the x-ray stop 419 is that the direct beam carries little information about the grain structure of the sample 10. Moreover, since its signal strength is much stronger than any diffracted beam, blocking the direct beam improves the performance of the projection plane x-ray detector 152 and reduces stray light generated in the scintillator 432 of the projection plane x-ray detector 152. In general, the size of the x-ray stop 419 is larger then the aperture 112 and the first x-ray stop 418 due to the diverging characteristic of the x-ray beam 115. However in other embodiments, the stop is 419 is attenuating, thus allowing the detector 152 to also detect the direct beam.

A projection detector stage 424 supports and is used to position the projection plane detector 152 along the beam axis 115.

In either case, the incoming diffraction x-ray beam 64 and transmitted (or extinction) x-ray beam 62 (if not blocked) are converted by the scintillator 432 of the projection plane x-ray detector 152 into photons of lower energy (typically within the visible range of the electromagnetic spectrum). In turn, the lower energy (typically in the visible region) photon beams emitted from transmitted direct x-ray image 62 and from diffracted x-ray image 64 are further handled by an optical portion 434 of the projection plane x-ray detector.

The optical portion 434 of the projection plane x-ray detector 152 can be much simpler than the Laue plane x-ray detector system 150. This is because, due to the geometrical magnification, the images are larger on the projection plane detector 152.

In one example, no optical magnification is provided. Instead a CCD panel detector is used directly after the scintillator 432. For example, a flat panel detector with 1:1 coupling to the scintillator 432 can be used. Such detectors have pixel sizes ranging typically from 50 µm to 250 µm.

In another example, optical portion 434 of the projection plane detector 152 has a visible light magnification of 0.4× and the CMOS sensor with a pixel size of 13 µm.

In one simple example, the Laue plane detector 150 and the projection plane detector 152 are the same physical detector. For each angle theta of the sample 10 relative to the beam, the detector is moved between the Laue plane 50 and the projection plane 52. This configuration requires a detector stage 422 with a large translation capability in the z and x axes.

In specific examples, the sample to projection detector distance dsd2 (also in the z direction) can be between 10 cm to 100 cm. The geometrical magnification of the x-rays at the projection plane detector 152 is preferably between 10 and 500.

The apparatus described herein also includes the system controller 105. The controller can be any processing unit suitable for carrying out the operations needed in order to obtain three dimensional crystallographic grain orientation mapping of the sample material. For instance, the controller 105 can be a computer system capable of receiving image data of multiple images from the detector systems 150, 152 (taken while rotating the sample 10) and for performing three dimensional reconstructions of grain orientation and position. In specific implementations, the controller 105 also controls the rotation stage 414 and thus the angle of rotation of the sample 10 being examined. Preferably, also the controller 105 operates the stages 422, 424 of the Laue plane detector 150 and the projection plane detector 152. And, specifically, the controller 105 moves the Laue plane detector 150 out of the optical path to enable detection by the projection plane detector 152, or moves the Laue plane detector 150 to the position of the projection plane detector 152 to perform its function.

In some cases, the controller 105 uses only data from the Laue detector 150 or only data from the projection plane data 152 to analyze the sample 10. In general, however, the information derived from the Laue detector 150 is most helpful in the analysis of the sample.

In many aspects of the invention, the controller 105 utilizes principles of x-ray DCT to generate a three dimensional crystallographic grain orientation mapping. Established DCT principles are described in several publications, all being incorporated herein by reference in their entirety. These publications are: W. Ludwig et al., *X-Ray Diffraction Contrast Tomography: A Novel Technique For Three-Dimensional Grain Mapping of Polycrystals. I. Direct Beam Case*, J. Appl. Cryst. (2008) V41, pp. 302-309 (Appendix A); G. Johnson et al., *X-Ray Diffraction Contrast Tomography: A Novel Technique For Three-Dimensional Grain Mapping of Polycrystals. II. The Combined Case*, J. Appl. Cryst. (2008) V41, pp. 310-318 (Appendix B); Martin Knapič, Seminar, 4$^{th}$ Year, University of Ljubljana, Facutly of Mathematics and Physics, Physics Department, May 28, 2011 (Appendix C); and U.S. Patent Application Publication No. 2012/0008736A1, to E. M. Lauridsen et al., published on Jan. 12, 2012 (Appendix D).

As described in the literature (see, e.g., Ludwig, et al. (2008). J. Appl. Cryst. 41, 302-309) x-ray DCT has some similarities to conventional X-ray absorption contrast tomography. Typically, grains in the sample are imaged using the occasionally occurring diffraction contribution to the X-ray attenuation coefficient each time a grain fulfils the diffraction condition. The three-dimensional grain shapes are reconstructed from a limited number of projections using an algebraic reconstruction technique (ART). Algorithms based on scanning orientation space and aiming at determining the corresponding crystallographic grain orientations also have been developed.

By simultaneous acquisition of the transmitted and the diffracted beams, the technique described by Ludwig, et al. (2008). J. Appl. Cryst. 41, 302-309 has been extended (see, e.g., G. Johnson et al., J. Appl. Cryst. (2008) V41, pp. 310-318) to the study of underformed polycrystalline samples containing more than 100 grains per cross section. Here, the grains are still imaged using the occasionally occurring diffraction contribution to the X-ray attenuation coefficient (which can be observed as a reduction in the intensity of the transmitted or direct beam 62 when a grain fulfils the diffraction condition). The segmentation of the extinction spot images with the additional diffracted beam information has been automated even in the presence of significant spot overlap. By pairing the corresponding direct ('extinction') and diffracted beam spots a robust sorting and indexing approach has been developed.

In general, with the present system, each grain in the sample 10 produces typically multiple, 1-20, diffraction spots or lines on the Laue detector 150 at every angle of the sample 10 to the x-ray beam axis 115. This effect can be used to eliminate the need for continuous rotation (theta) of the sample 10. Additionally, the line geometry of the diffraction spots in the Laue plane reduces the "overlap" problem since the lines can be separated more easily than large spots, which are detected with traditional systems.

In one embodiment, data from regions 60, 62, and 64 detected by the Laue detector 150 and the projection plane detector 152 are communicated with the controller 105. Besides receiving signals from transmitted image 62 and diffraction spots 60, 64 from diffracted image, the controller 105 preferably also controls the sample stage 414 so that the crystalline material sample 10 is automatically rotated during the exposure process.

While this invention has been particularly shown and described with references to preferred embodiments thereof, it will be understood by those skilled in the art that various changes in form and details may be made therein without departing from the scope of the invention encompassed by the appended claims.

For example, use of a broadband x-ray spectrum for DCT has not been considered at synchrotron radiation sources. If a synchrotron beam would be conditioned to deliver a diverging broadband beam to a polycrystalline sample, the same methods as described above can be employed potentially offering significant performance advantages over the currently used methods, which use a monochromatic beam. In fact, underutilized, low-brightness bending magnet beamlines at synchrotrons could be used instead of a laboratory source to provide the broadband, divergent x-ray beam.

What is claimed is:

1. A method for three dimensional crystallographic grain orientation mapping, the method comprising:
    illuminating a rotating polycrystalline sample with a broadband x-ray beam derived from a laboratory x-ray source;
    detecting, on one or more x-ray detectors, diffracted beams from the sample; and
    processing data from said diffracted beams with the sample in different rotation positions to generate three dimensional reconstructions of grain orientation, position, and/or 3-D volume.

2. The method of claim 1, wherein, before illuminating the sample, the x ray beam generated by the laboratory x-ray source is passed through an aperture that controls beam divergence.

3. The method of claim 1, wherein, before illuminating the sample, the beam generated by the laboratory x-ray source is filtered to control its bandwidth.

4. The method of claim 1, wherein, after being transmitted through the sample, the beam generated by the laboratory x-ray source is filtered to remove unwanted energies in the x-ray beam.

5. The method of claim 1, wherein the beam that illuminates the sample is a cone beam.

6. The method of claim 1, wherein the beam that illuminates the sample is an unfocused x-ray beam.

7. The method of claim 1, wherein the one or more x-ray detectors comprise a high resolution pixilated x-ray detector to collect diffracted x-rays and generate diffraction data and a lower resolution detector to detect projection images through the sample.

8. The method of claim 1, further comprising positioning an x-ray detector at a Laue focal plane.

9. The method of claim 1, further comprising generating the broadband x-ray beam by irradiating a Tungsten, Molybdenum, Gold, Platinum, Silver, or Copper target with an electron beam.

10. The method of claim 1, further comprising conditioning the x-ray beam that illuminates the sample with a spectral filter that reduces a total power in the beam by no greater than 50%.

11. The method of claim 1, further comprising rotating the sample in stepwise, incremental rotational movements in the range from 0.01° to 15° per incremental rotation.

12. The method of claim 1, further comprising providing an x-ray stop to block or attenuate a direct beam from the x-ray source from reaching an x-ray detector.

13. The method of claim 1, wherein a ratio of a full width half maximum (FWHM) of the broadband x-ray beam to a central x-ray energy of the broadband x-ray beam is greater than 20%.

14. The method of claim 1, wherein a ratio a full width half maximum (FWHM) of the broadband x-ray beam to a central x-ray energy of the broadband x-ray beam is greater than 40%.

15. The method of claim 1, wherein the x-ray beam is diverging from the x-ray source and is focused in a diffraction plane by grains within the sample.

16. An apparatus for conducting three dimensional crystallographic grain orientation mapping, comprising:
    a laboratory x-ray source generating a broadband x-ray beam;
    a sample rotation stage for rotating the sample in the x-ray beam;
    at least one x-ray detector to collect diffraction data from the sample; and
    a controller for receiving the diffraction data from the detector for different rotation positions of the sample and performing three dimensional reconstructions of grain orientation and position.

17. The apparatus of claim 16, further comprising a beam defining aperture for limiting an illuminated area on the sample and restricting the size of a direct beam on the detector.

18. The apparatus of claim 16, wherein the detector comprises a scintillator and an optical portion for magnifying and collecting photons generated from the scintillator by the broadband x ray beam diffracted by the sample.

19. The apparatus of claim 16, further comprising a spectral filter that reduces a bandwidth of the x-ray beam that illuminates the sample.

20. The apparatus of claim 16, wherein the beam that illuminates the sample is a cone beam.

21. The apparatus of claim 16, wherein the beam that illuminates the sample is an unfocused x-ray beam.

22. The apparatus of claim 16, wherein the at least one x-ray detector comprises a high resolution pixilated x-ray detector to collect diffracted x-rays and generate diffraction data and a lower resolution detector to detect projection images through the sample.

23. The apparatus of claim 16, wherein the at least one x-ray detector comprises an x-ray detector at a Laue focal plane.

24. The apparatus of claim 16, wherein the laboratory x-ray source generates the broadband x-ray beam by irradiating a Tungsten, Molybdenum, Gold, Platinum, Silver or Copper target with an electron beam.

25. The apparatus of claim 16, wherein the sample rotation stage rotates the sample in stepwise, incremental rotational movements in the range from 0.01° to 15° per incremental rotation.

26. The apparatus of claim 16, further comprising an x-ray stop to block or attenuate a direct beam from the x-ray source from reaching an x-ray detector.

27. The apparatus of claim 16, wherein a ratio of a full width half maximum (FWHM) of the broadband x-ray beam to a central x-ray energy of the broadband x-ray beam is greater than 20%.

28. The apparatus of claim 16, wherein a ratio a full width half maximum (FWHM) of the broadband x-ray beam to a central x-ray energy of the broadband x-ray beam is greater than 40%.

29. The apparatus of claim 16, wherein the x-ray beam is diverging from the x-ray source and is focused in a diffraction plane by grains within the sample.

30. A projection x-ray imaging system for three dimensional crystallographic grain orientation mapping, comprising:
    a laboratory x-ray source for generating a broadband x ray beam;
    a beam defining aperture that limits the illuminated area on the sample and restricts the size of the direct beam;
    a sample motion stage system with a rotation stage to acquire a series of angular projections;
    at least one detector to collect diffraction data; and
    a controller that receives diffraction data from the detector and performing three dimensional reconstructions of grain orientation and position.

31. A projection x-ray imaging system for three dimensional crystallographic grain orientation mapping, comprising:
    an x-ray source for generating a diverging x ray beam;
    a sample rotation stage for rotating the sample in the x-ray beam;
    at least one x-ray detector to collect diffraction information by detecting diffracted x-rays from the sample that have been focused in a diffraction plane direction by grains within the sample; and
    a controller for receiving the diffraction information from the detector for different rotation positions of the sample and performing three dimensional reconstructions of grain orientation and position.

* * * * *